(12) United States Patent
Finkelstein

(10) Patent No.: US 7,692,009 B2
(45) Date of Patent: *Apr. 6, 2010

(54) REFERENCE STANDARD FOR CHARACTERIZATION OF ROSUVASTATIN

(75) Inventor: Nina Finkelstein, Herzliya (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/823,019

(22) Filed: Jun. 25, 2007

(65) Prior Publication Data

US 2007/0249830 A1 Oct. 25, 2007

Related U.S. Application Data

(62) Division of application No. 11/001,912, filed on Dec. 2, 2004, now Pat. No. 7,244,844.

(60) Provisional application No. 60/526,449, filed on Dec. 2, 2003.

(51) Int. Cl.
  C07D 239/70 (2006.01)
  C07D 405/02 (2006.01)
  A61K 31/517 (2006.01)
  A61P 3/06 (2006.01)

(52) U.S. Cl. ...................................... 544/249; 514/267

(58) Field of Classification Search .................. 544/249
  See application file for complete search history.

(56) References Cited

U.S. PATENT DOCUMENTS

| | | | |
|---|---|---|---|
| 4,231,938 A | 11/1980 | Monaghan et al. | |
| 4,346,227 A | 8/1982 | Terahara et al. | |
| 4,444,784 A | 4/1984 | Hoffman et al. | |
| 4,739,073 A | 4/1988 | Kathawala | |
| 5,006,530 A | 4/1991 | Angerbauer et al. | |
| 5,177,080 A | 1/1993 | Angerbauer et al. | |
| 5,260,440 A | 11/1993 | Hirai et al. | |
| 5,354,879 A | 10/1994 | Konoike et al. | |
| RE37,314 E | 8/2001 | Hirai et al. | |
| 6,316,460 B1 | 11/2001 | Creekmore et al. | |
| 6,333,198 B1 | 12/2001 | Edmeades et al. | |
| 6,777,552 B2 | 8/2004 | Niddam-Hildesheim et al. | |
| 6,858,618 B2 | 2/2005 | Raza et al. | |
| 2005/0131066 A1 | 6/2005 | Niddam-Hildesheim et al. | |
| 2005/0222415 A1 | 10/2005 | Kumar et al. | |
| 2007/0191318 A1 | 8/2007 | Kumar et al. | |

FOREIGN PATENT DOCUMENTS

| EP | 0 850 902 | 7/1998 |
|---|---|---|
| EP | 0 521 471 | 10/2000 |
| WO | WO 00/17150 | 3/2000 |
| WO | WO 00/49014 A | 8/2000 |
| WO | WO 01/60804 | 8/2001 |
| WO | WO 03/016317 | 2/2003 |
| WO | WO 03/032995 | 4/2003 |
| WO | WO 03/087112 | 10/2003 |
| WO | WO 03/097614 A | 11/2003 |
| WO | WO 2004/014872 | 2/2004 |
| WO | WO 2004/052867 | 6/2004 |
| WO | WO 2005/021511 | 3/2005 |
| WO | WO 2006/035277 | 4/2006 |
| WO | WO 2006/079611 | 8/2006 |
| WO | WO 2006 100689 | 9/2006 |
| WO | WO 2006/106526 | 10/2006 |
| WO | WO 2006/136407 | 12/2006 |
| WO | WO 2006/136408 | 12/2006 |
| WO | WO 2007/007119 | 1/2007 |

OTHER PUBLICATIONS

Anelli, et al., "Fast and Selective Oxidation of Primary Alcohols to Aldehydes or to Carboxylic Acids and of Secondary Alcohols to Ketones Mediated by Oxoammonium Salts Under Two-Phase Conditions", *J. Org. Chem.*, 1987, pp. 2559-2562, vol. 52, No. 12.

Hull, et al., "Quantification of Rosuvastatin in Human Plasma by Automated Solid-Phase Extraction Using Tandem Mass Spectrometric Detection", *Journal of Chromatography B: Biomedical Sciences & Applications*, 2002, pp. 219-228, vol. 772, No. 2.

Konoike, et al. "Practical Synthesis of Chiral Synthons for the Preparation of HMG-CoA Reductase Inhibitors" *J. Org. Chem.*, vol. 59, 1994, pp. 7849-7854.

Lenz, et al., "Tetra-$N$-Propylammonium Perruthenate (TPAP)-Catalysed Oxidations of Alcohols Using Molecular Oxygen As a Co-Oxidant", *J. Chem. Soc., Perkin Trans. 1*, 1997, 3291-3292.

Ley, et al., *Synthesis*, 1994, 639-666.

Lipid Research Clinics Program, "The Lipid Research Clinics Coronary Primary Prevention Trial Results: I. Reduction in Incidence of Coronary Heart Disease", *J.A.M.A.*, 1984, 351-74, vol. 251, No. 3.

Scandinavian Simvastatin Survival Study Group, "Randomised Trial of Cholesterol Lowering in 4444 Patients With Coronary Heart Disease: The Scandinavian Survival Study (4s)", *The Lancet*, 1994, pp. 1383-1389, vol. 344.

Snyder, et al., *Introduction to Modern Liquid Chromatography, 2nd ed.*, John Wiley & Sons: New York, 1979, pp. 549, 552, 571-572.

Strobel, et al., *Chemical Instrumentation: A Systematic Approach, 3rd ed.*, Wiley & Sons: New York, 1989, pp. 391-393, 879, 894, 922, 924-925, 953.

Wantanabe, et al., "Synthesis and Biological Antivity of Methanesulfonamide Pyramidine-And N-Methanesulfonyl Pyrrole-Substituted 3,5-Dihydroxy-6-Heptenoates, A Novel Series of HMG-CoA Reductase Inhibitors", *Bioorganic & Medicinal Chemistry*, 1997, pp. 437-444, vol. 5, No. 2.

Witztum, "Chapter 36: Drugs Used in the Treatment of Hyperlipoproteinemias", *Goodman & Gilman's The Pharmacological Basis of Therapeutics*, 9th ed., pp. 875-897.

*Primary Examiner*—Venkataraman Balasubramanian
(74) *Attorney, Agent, or Firm*—Kenyon & Kenyon LLP

(57) ABSTRACT

Provided are rosuvastatin degradation products and their use as a reference standard (including reference marker) for analysis of rosuvastatin.

2 Claims, 7 Drawing Sheets

HPLC CHROMATOGRAM OF A MIXTURE OF ROSUVASTATIN, COMPOUND VI, COMPOUND VII

D-2500
METHOD: ROSUVASTATIN  TAG: 12  CH: 1
FILE: 0  CALC-METHOD: AREA %  TABLE: 0  CONC: AREA

| NO. | RT | AREA | CONC | BC |
|---|---|---|---|---|
| 1 | 2.59 | 18433 | 3.611 | BB |
| 4 | 4.12 | 10807 | 2.117 | BB |
| 8 | 8.14 | 53524 | 10.485 | VB |
| 11 | 10.00 | 20230 | 3.963 | BB |
| 12 | 10.84 | 199132 | 39.008 | BB |
| 13 | 11.78 | 208366 | 40.817 | BB |
| TOTAL | | 510492 | 100.000 | |
| PEAK PEJ : | | 10000 | | |

Chromatogram of Purity of Compound VI

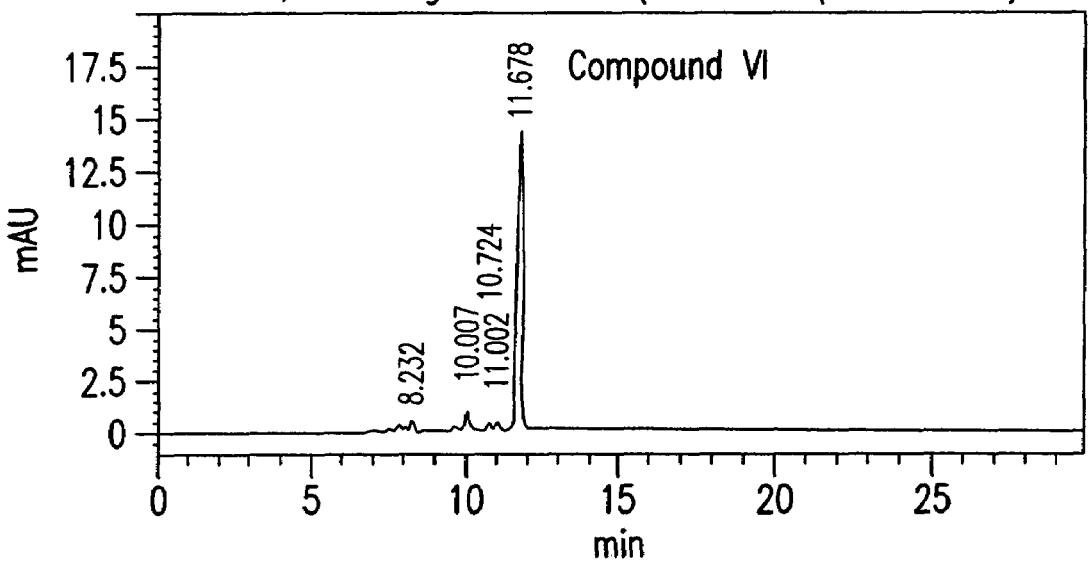

```
===================================================
                   Area Percent Report
===================================================
Sorted By         :        Signal Multiplier        :        1.0000
Dilution          :        1.0000
Use Multiplier & Dilution Factor with ISTDs Signal 1: VWD1 A, Wavelength=245 nm Peak RetTime Type  Width    Area      Area     Name
 #   (min)        (min)    mAU *s     %
---|-------|----|-------|---------|--------|-------------
 1   8.232  BB   0.1319   4.08695   2.4642
 2  10.007  BB   0.1581   9.56191   5.7653
 3  10.724  BB   0.1261   2.32142   1.3997   Compound VII
 4  11.002  BB   0.1280   2.47210   1.4905
 5  11.678  PBA  0.1609 147.41133  88.8803   Compound VI
Totals :                 165.85372
```

FIG.4

Chromatogram of Purity of Compound VII

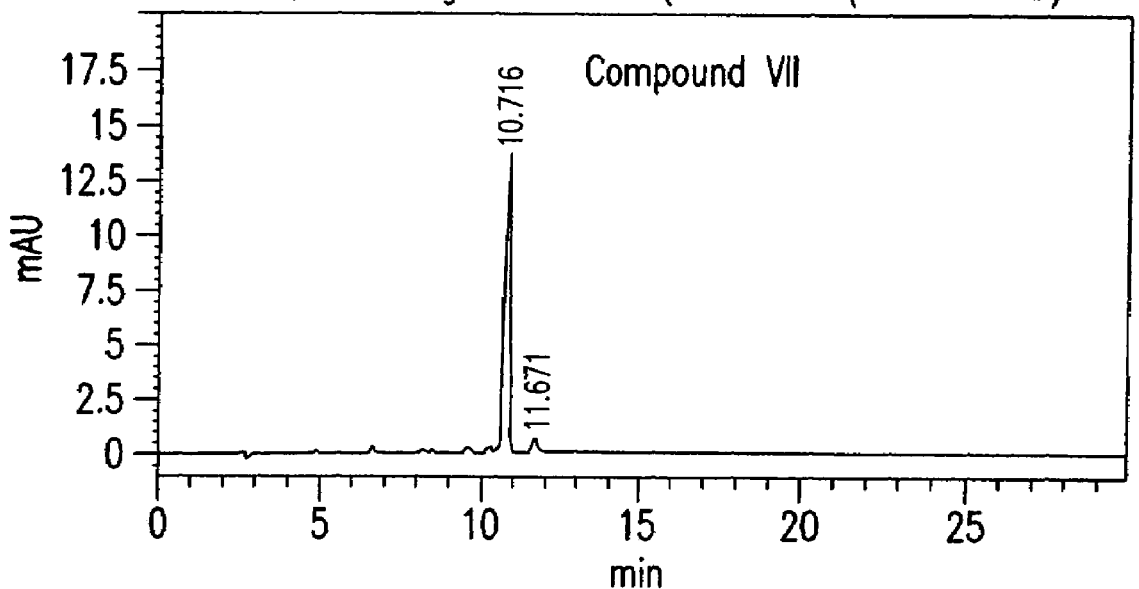

```
===============================================
              Area Percent Report
===============================================
Sorted By            :      Signal Multiplier           :      1.0000
Dilution             :      1.0000
Use Multiplier & Dilution Factor with ISTDs Signal 1: VWD1 A, Wavelength=245 nm Peak RetTime Type  Width     Area       Area     Name
 #   (min)        (min)    mAU *s       %
---|-------|----|-------|----------|---------|------------
 1   8.234        0.0000   0.00000    0.000    Rosu-Ca
 2  10.716  PBA   0.1546  136.96135  95.0156   Compound VII
 3  11.671  BB    0.1459    7.18489   4.9844   Compound VI
Totals :                  144.14624
```

FIG.5

Chromatogram of mixture of Rosuvastatin Ca, Compound VI and Compound VII

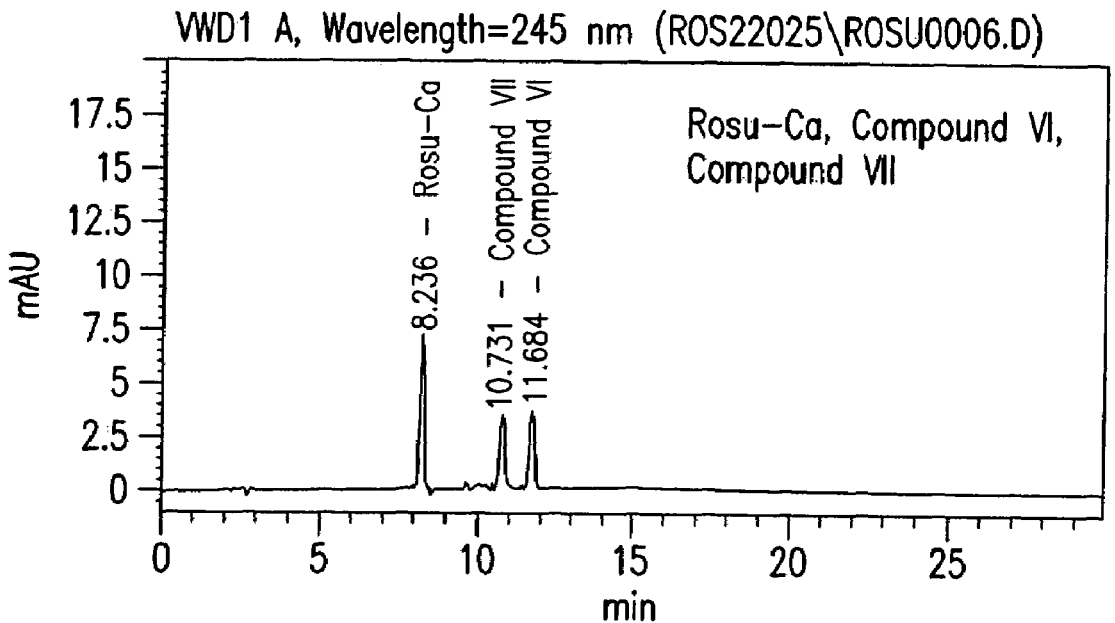

```
=====================================================
                    Area Percent Report
=====================================================
```

Sorted By         :    Signal

Multiplier        :    1.0000
Dilution          :    1.0000
Use Multiplier & Dilution Factor with ISTDs Signal 1:  VWD1 A, Wavelength=245 nm

| Peak # | RetTime (min) | Type | Width (min) | Area mAU *s | Area % | Name |
|---|---|---|---|---|---|---|
| 1 | 8.236 | BBA | 0.1353 | 62.72866 | 46.6302 | Rosu-Ca |
| 2 | 10.731 | BBA | 0.1532 | 33.78985 | 25.1181 | Compound VII |
| 3 | 11.684 | BB | 0.1606 | 38.00530 | 28.2517 | Compound VI |
| Totals : | | | | 134.52381 | | |

FIG.6

Chromatogram of Rosuvastatin Ca spiked with Compound VI and Compound VII

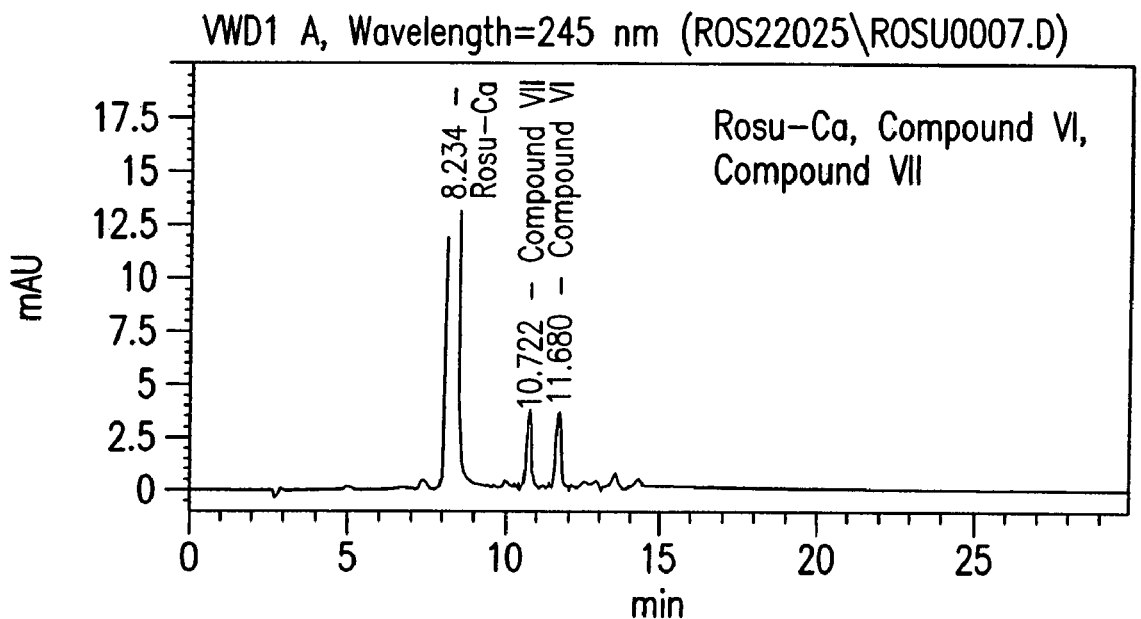

```
=====================================================
                     Area Percent Report
=====================================================
```

Sorted By          :    Signal

Multiplier         :    1.0000
Dilution           :    1.0000
Use Multiplier & Dilution Factor with ISTDs Signal 1: VWD1 A, Wavelength=245 nm

| Peak # | RetTime (min) | Type | Width (min) | Area mAU *s | Area % | Name |
|---|---|---|---|---|---|---|
| 1 | 8.234 | BBA | 0.1366 | 1.18296e4 | 99.3533 | Rosu-Ca |
| 2 | 10.722 | BBA | 0.1569 | 37.81250 | 0.3176 | Compound VII |
| 3 | 11.680 | BB | 0.1624 | 39.18864 | 0.3291 | Compound VI |
| Totals : | | | | 1.19066e4 | | |

FIG.7

REFERENCE STANDARD FOR CHARACTERIZATION OF ROSUVASTATIN

CROSS-REFERENCE TO RELATED APPLICATIONS

This application is a divisional of U.S. application Ser. No. 11/001,912, filed Dec. 2, 2004, now U.S. Pat. No. 7,244,844, which claims the benefit of U.S. Provisional Application No. 60/526,449 filed on Dec. 2, 2003, the disclosure of which is incorporated by reference in its entirety herein.

FIELD OF THE INVENTION

The present invention relates to rosuvastatin degradation products and their use as a reference standard for analysis of rosuvastatin.

BACKGROUND OF THE INVENTION

Statins are currently the most therapeutically effective drugs available for reducing low-density lipoprotein (LDL) particle concentration in the blood stream of patients at risk for cardiovascular disease. Thus, statins are used in the treatment of hypercholesterolemia, hyperlipoproteinemia, and atherosclerosis. A high level of LDL in the bloodstream has been linked to the formation of coronary lesions that obstruct the flow of blood and can rupture and promote thrombosis. Goodman and Gilman, The Pharmacological Basis of Therapeutics, page 879 (9th Ed. 1996).

Statins inhibit cholesterol biosynthesis in humans by competitively inhibiting the 3-hydroxy-3-methyl-glutaryl-coenzyme A ("HMG-CoA") reductase enzyme. HMG-CoA reductase catalyzes the conversion of HMG to mevalonate, which is the rate-determining step in the biosynthesis of cholesterol. Decreased production of cholesterol causes an increase in the number of LDL receptors and corresponding reduction in the concentration of LDL particles in the bloodstream. Reduction in the LDL level in the bloodstream reduces the risk of coronary artery disease. J.A.M.A. 1984, 251, 351-74.

Currently available statins include lovastatin, simvastatin, pravastatin, fluvastatin, cerivastatin and atorvastatin. Lovastatin (disclosed in U.S. Pat. No. 4,231,938) and simvastatin (disclosed in U.S. Pat. No. 4,444,784) are administered in the lactone form. After absorption, the lactone ring is opened in the liver by chemical or enzymatic hydrolysis, and the active hydroxy acid is generated. Pravastatin (disclosed in U.S. Pat. No. 4,346,227) is administered as the sodium salt. Fluvastatin (disclosed in U.S. Pat. No. 4,739,073) and cerivastatin (disclosed in U.S. Pat. Nos. 5,006,530 and 5,177,080), also administered as the sodium salt, are entirely synthetic compounds that are in part structurally distinct from the fungal derivatives of this class that contain a hexahydronaphthalene ring. Atorvastatin and two new "superstatins," rosuvastatin and pitavastatin, are administered as calcium salts.

Rosuvastatin calcium (monocalcium bis (+) 7-[4-(4-fluorophenyl)-6-isopropyl-2-(N-methyl-N-methylsulfonylaminopyrimidin)-5-yl]-(3R,5S)-dihydroxy-(E)-6-heptenoate) is an HMG-CoA reductase inhibitor, developed by Shionogi for the once daily oral treatment of hyperlipidaemia (Ann Rep, Shionogi, 1996; Direct communications, Shionogi, 8 Feb. 1999 & 25 Feb. 2000). Rosuvastatin calcium is a superstatin, which can lower LDL-cholesterol and triglycerides more effectively than first generation drugs. Rosuvastatin calcium has the following chemical formula:

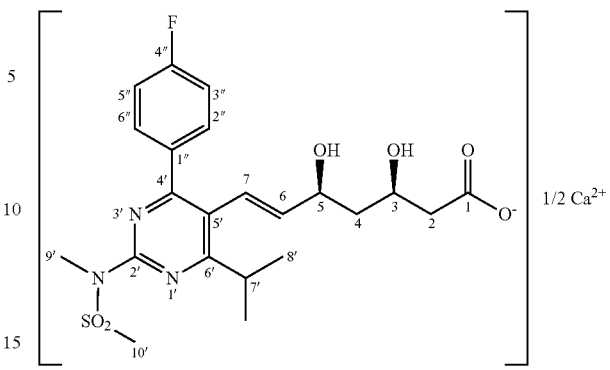

Rosuvastatin calcium is marketed under the name CRESTOR for treatment of a mammal such as a human. According to the maker of CRESTOR, it is administered in a daily dose of from about 5 mg to about 40 mg. For patients requiring less aggressive LDL-C reductions or who have pre-disposing factors for myopathy, the 5 mg dose is recommended, while 10 mg dose is recommended for the average patient, 20 mg dose for patients with marked hyper-cholesterolemia and aggressive lipid targets (>190 mg/dL), and the 40 mg dose for patients who have not been responsive to lower doses.

U.S. Pat. No. 5,260,440 discloses and claims rosuvastatin, its calcium salt (2:1), and its lactone form. The process of the '440 patent prepares rosuvastatin by reacting 4-(4-fluorophenyl)-6-isopropyl-2-(N-methyl-N-methylsulfonylamino)-5-pyrimidinecarbaldehyde with methyl (3R)-3-(tert-butyldimethylsilyloxy)-5-oxo-6-triphenylphosphoranylidene hexanate in acetonitrile under reflux. The silyl group is then cleaved with hydrogen fluoride, followed by reduction with $NaBH_4$ and diethylmethoxyborane in THF to obtain a methyl ester of rosuvastatin.

The ester is then hydrolyzed with sodium hydroxide in ethanol at room temperature, followed by removal of ethanol and addition of ether, to obtain the sodium salt of rosuvastatin. The sodium salt is then converted to the calcium salt. The sodium salt is dissolved in water and maintained under a nitrogen atmosphere. Calcium chloride is then added to the solution, resulting in precipitation of rosuvastatin calcium (2:1). The process for preparation of the intermediates disclosed in the '440 patent is incorporated herein by reference.

U.S. Pat. No. 6,316,460 discloses a pharmaceutical composition of rosuvastatin. The pharmaceutical compositions contain rosuvastatin or its salt and a multivalent tribasic phosphate salt.

The product mixture of a reaction rarely is a single compound pure enough to comply with pharmaceutical standards. Side products and byproducts of the reaction and adjunct reagents used in the reaction will, in most cases, be present. At certain stages during processing of the rosuvastatin contained in the product mixture into an active pharmaceutical ingredient ("API"), the rosuvastatin must be analyzed for purity, typically by HPLC or GC analysis, to determine if it is suitable for continued processing or ultimately for use in a pharmaceutical product. The rosuvastatin does not need to be absolutely pure. Absolute purity is a theoretical ideal that is unattainable. Rather, there are purity standards intended to ensure that an API is not made less safe for clinical use because of the presence of impurities. In the United States, the Food and Drug Administration guidelines recommend that applicants limit some impurities to below 0.1%.

Generally, side products, byproducts and adjunct reagents (collectively "impurities") are identified spectroscopically and by other physical methods and then the impurities are associated with a peak position in a chromatogram (or a spot on a TLC plate). (Strobel p. 953) (Strobel, H. A.; Heineman, W. R., *Chemical Instrumentation: A Systematic Approach*, $3^{rd}$ dd. (Wiley & Sons: New York 1989)). Thereafter, the impurity can be identified by its position in the chromatogram, which is conventionally measured in minutes between injection of the sample on the column and elution of the particular component through the detector, known as the "retention time." This time period varies daily based upon the condition of the instrumentation and many other factors. To mitigate the effect that such variations have upon accurate identification of an impurity, practitioners use "relative retention time" ("RRT") to identify impurities. (Strobel p. 922). The RRT of an impurity is its retention time divided by the retention time of some reference marker. In theory, rosuvastatin itself could be used as the reference marker, but as a practical matter it is present in such overwhelming proportion in the mixture that it tends to saturate the column, leading to irreproducible retention times, i.e., the maximum of the peak corresponding to rosuvastatin tends to wander (Strobel FIG. 24.8(b) p. 879, contains an illustration of the sort of asymmetric peak that is observed when a column is overloaded). Thus, it is sometimes desirable to select an alternative compound that is added to, or is present in, the mixture in an amount significant enough to be detectable and sufficiently low as not to saturate the column and to use that compound as the reference marker.

Researchers and developers in drug manufacturing understand that a compound in a relatively pure state can be used as a "reference standard" (a "reference marker" is similar to a reference standard but it is used for qualitative analysis) to quantify the amount of the compound in an unknown mixture. When the compound is used as an "external standard," a solution of a known concentration of the compound is analyzed by the same technique as the unknown mixture. (Strobel p. 924, Snyder p. 549) (Snyder, L. R.; Kirkland, J. J. *Introduction to Modern Liquid Chromatography*, 2nd ed. (John Wiley & Sons: New York 1979)). The amount of the compound in the mixture can be determined by comparing the magnitude of the detector response. See also U.S. Pat. No. 6,333,198, incorporated herein by reference.

The reference standard compound also can be used to quantify the amount of another compound in the mixture if the "response factor," which compensates for differences in the sensitivity of the detector to the two compounds, has been predetermined. (Strobel p. 894). For this purpose, the reference standard compound may be added directly to the mixture, in which case it is called an "internal standard." (Strobel p. 925, Snyder p. 552).

The reference standard compound can even be used as an internal standard when the unknown mixture contains some of the reference standard compound by using a technique called "standard addition," wherein at least two samples are prepared by adding known and differing amounts of the internal standard. (Strobel pp. 391-393, Snyder pp. 571, 572). The proportion of detector response due to the reference standard compound that is originally in the mixture can be determined by extrapolation of a plot of detector response versus the amount of the reference standard compound that was added to each of the samples to zero. (e.g. Strobel, FIG. 11.4 p. 392).

The present invention provides a rosuvastatin degradation product that can be used as a reference standard for analysis of rosuvastatin.

SUMMARY OF THE INVENTION

In one aspect, the present invention provides a rosuvastatin degradation product having the following structure:

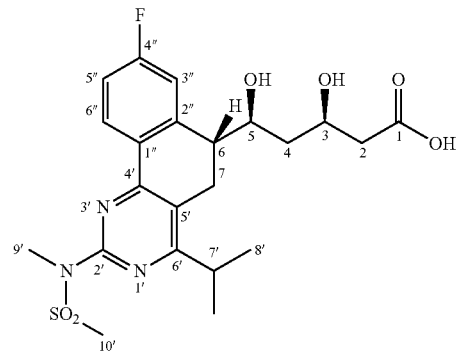

In another aspect, the present invention provides a rosuvastatin degradation product having the following structure:

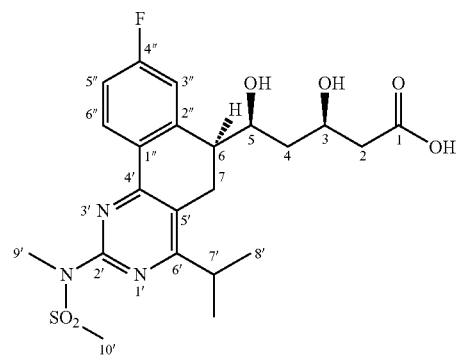

In another aspect, the present invention provides a rosuvastatin degradation product having the following structure:

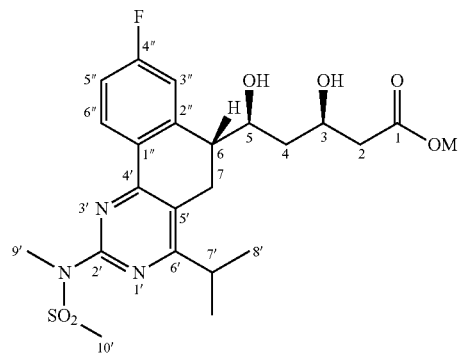

wherein M is an alkali or alkaline earth metal.

In another aspect, the present invention provides a rosuvastatin degradation product having the following structure:

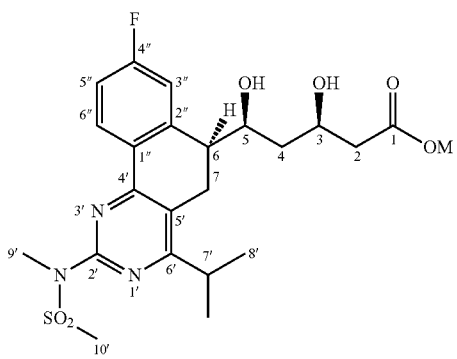

wherein M is an alkali or alkaline earth metal. Preferably M is calcium. The calcium salt may be converted to lactone form by combining it with acetonitrile and hydrochloric acid; or to free acid comprising dissolving the calcium salt in a mixture of acetonitrile and water, and contacting the calcium salt with a silica column.

In another aspect the present invention provides a lactone form of a rosuvastatin degradation product having the following structure:

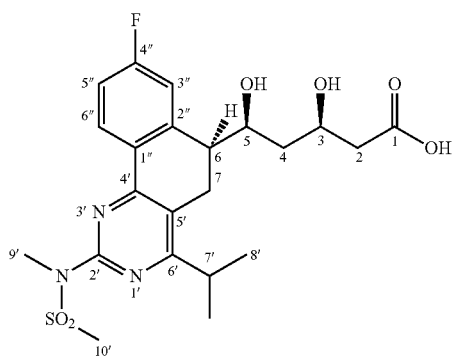

wherein, in the lactone form. $C^1$ and $C^5$ form an ester derivative of formula:

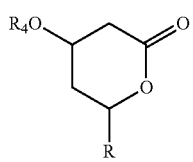

wherein $R_4$ is a hydrogen and R represents the rest of the structure of the rosuvastatin degradation product.

In another aspect, the present invention provides a lactone form of a rosuvastatin degradation product having the following structure:

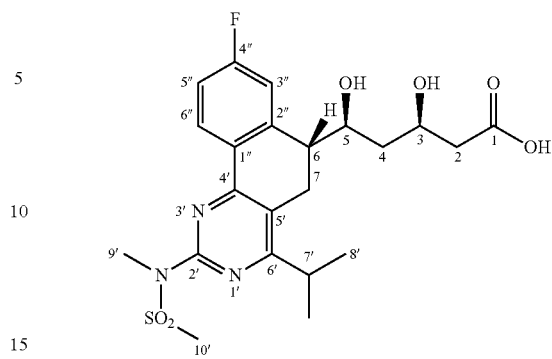

wherein, in the lactone form. $C^1$ and $C^5$ form an ester derivative of formula:

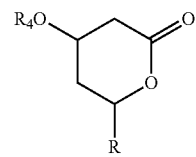

wherein $R_4$ is a hydrogen and R represents the rest of the structure of the rosuvastatin degradation product.

In another aspect, the present invention provides a process for converting the lactone to free acid form comprising hydrolyzing the lactone under aqueous basic conditions to obtain a metal salt and contacting the metal salt with a silica column.

Preferably the degradation product is about 95% free % area by HPLC of its corresponding stereoisomer at position 6. The rosuvastatin degradation product may be isolated or purified.

In another aspect, the present invention provides a method for analyzing a sample of rosuvastatin comprising the steps of:

a) performing chromatography on the sample to obtain data; and b) comparing the data with the chromatography data of the degradation product.

In another aspect the present invention provides a process for preparing the degradation product comprising the step of irradiating with visible light rosuvastatin acid, rosuvastatin alkali or alkaline earth metal salt or rosuvastatin lactone.

In another aspect, the present invention provides a method for determining the retention time of a chromatography column for rosuvastatin, comprising the steps of carrying out chromatography with the following compound as a standard,

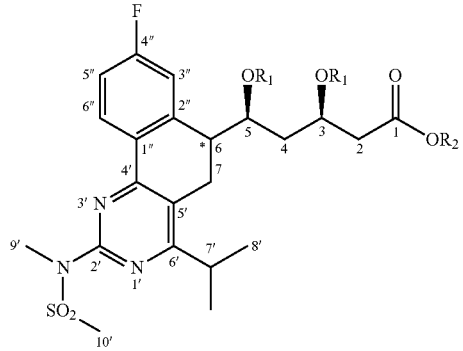

wherein $R_1$ and $R_2$ are independently hydrogen or a hydrolyzable protecting group; $R_3$ is hydrogen, a $C_1$ to $C_4$ alkyl group, or an alkali or alkaline earth metal; or wherein $C^1$ and $C^5$ form a lactone.

BRIEF DESCRIPTION OF THE FIGURES

FIG. 4 is an HPLC chromatogram of the Purity of Compound VI.

FIG. 5 is a chromatogram of purity of Compound VII.

FIG. 6 is a chromatogram of a mixture of rosuvastatin Ca, Compound VI and Compound VII.

FIG. 7 is a chromatogram of rosuvastatin Ca spiked with Compound VI and Compound VII.

DETAILED DESCRIPTION OF THE INVENTION

Figure 1:
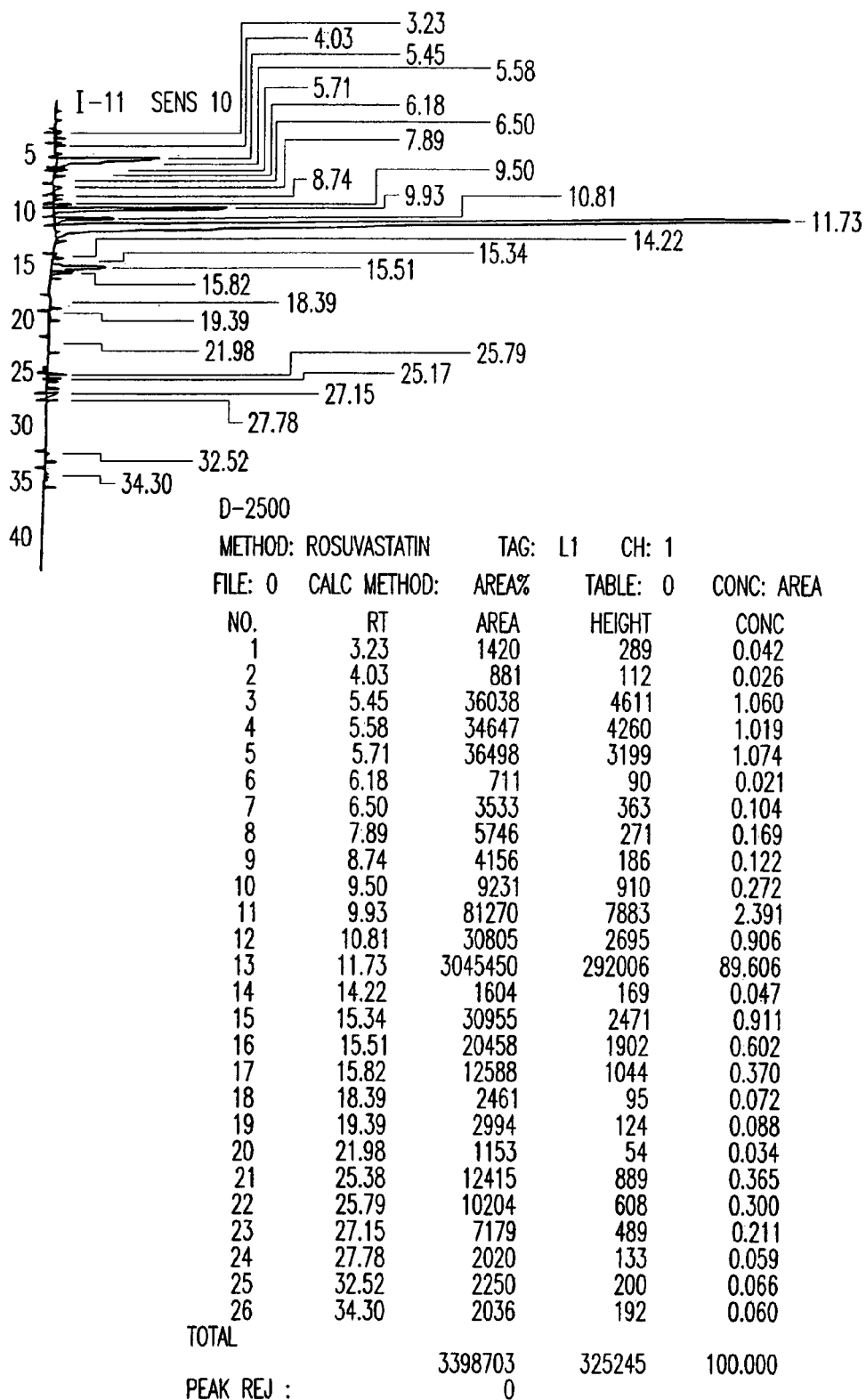
FIG. 1 is an HPLC chromatogram of Compound VI.
Figure 2:
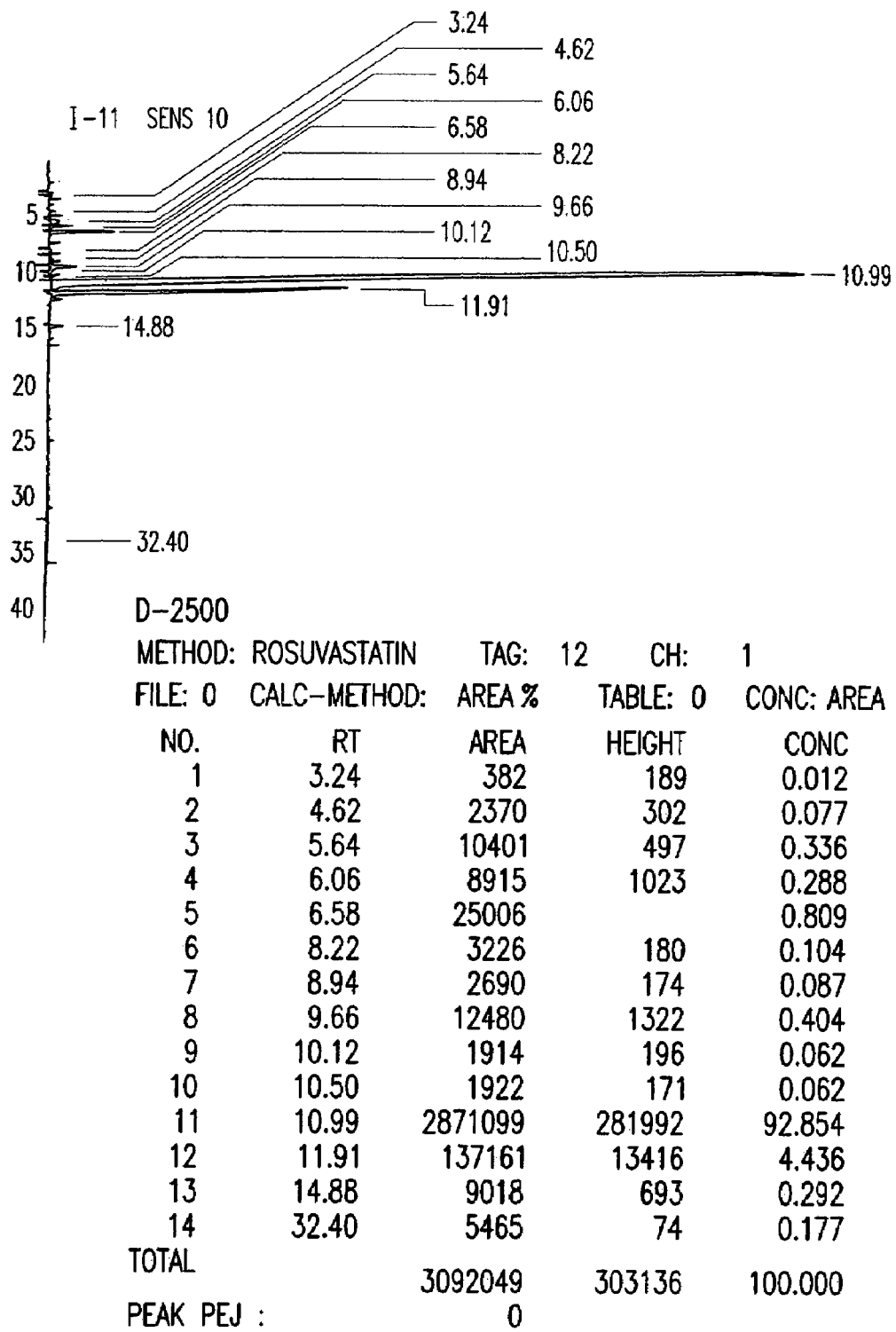
FIG. 2 is an HPLC chromatogram of Compound VII.
Figure 3:
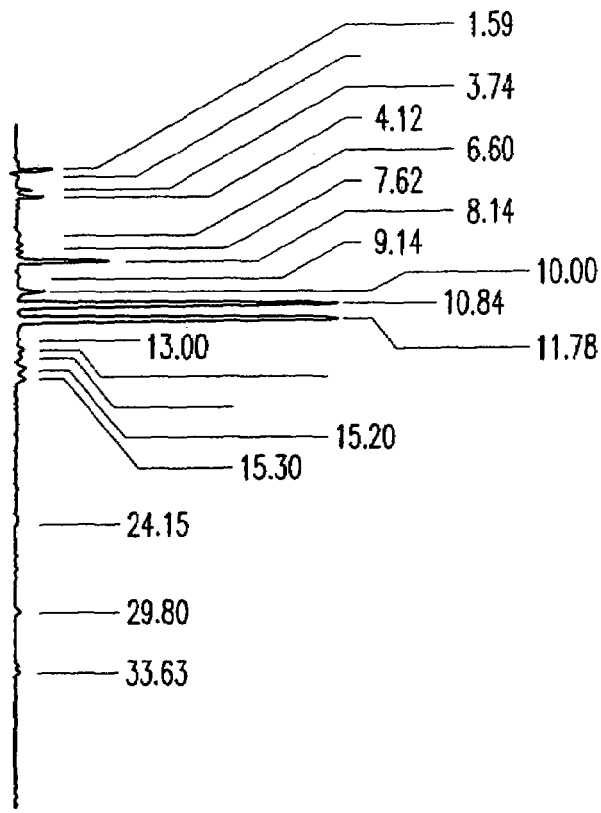
FIG. 3 is an HPLC chromatogram of a mixture of rosuvastatin, Compound VI, and Compound VII.

As used herein, the term "reference standard" refers to a compound that may be used both for quantitative and qualitative analysis of an active pharmaceutical ingredient. For example, the retention time of the compound in HPLC allows for setting a relative retention time, thus making qualitative analysis possible. The concentration of the compound in solution before injection into an HPLC column allows for comparison of the areas under the peaks in an HPLC chromatogram, thus making quantitative analysis possible.

A "reference marker" is used in qualitative analysis to identify components of a mixture based upon their position, e.g. in a chromatogram or on a Thin Layer Chromatography (TLC) plate (Strobel pp. 921, 922, 953). For this purpose, the compound does not necessarily have to be added to the mixture if it is present in the mixture. A "reference marker" is used only for qualitative analysis, while a reference standard may be used for quantitative or qualitative analysis, or both. Hence, a reference marker is a subset of a reference standard, and is included within the definition of a reference standard.

Although some of the knowledge of those in the art regarding reference standards has been described in general terms up to this point, those skilled in the art also understand that the detector response can be, for example, the peak heights or integrated peak areas of a chromatogram obtained, e.g. by UV or refractive index detection, from the eluent of an HPLC system or, e.g. flame ionization detection or thermal conductivity detection, from the eluent of a gas chromatograph, or other detector response, e.g. the UV absorbence, of spots on a fluorescent TLC plate. The position of the reference standard may be used to calculate the relative retention time for rosuvastatin and other impurities.

When rosuvastatin calcium is exposed to visible light irradiation, degradation products of rosuvastatin are obtained, which can be used as a reference standard. The two degradation products are diastereomeric cyclic products (II) and (III) with the creation of an additional asymmetric center in position 6 as follows:

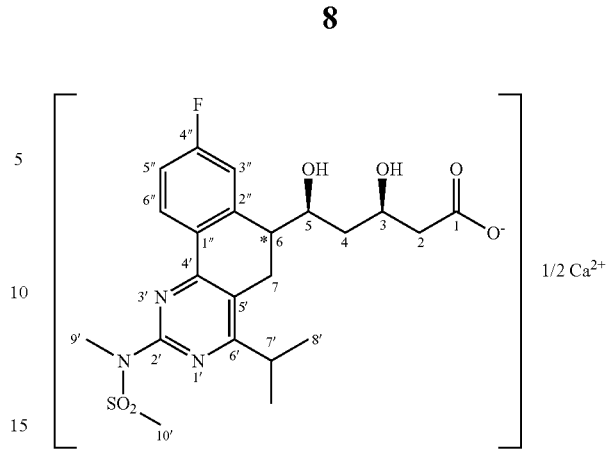

In addition to rosuvastatin calcium, other forms of rosuvastatin may be irradiated, including the lactone, free acid and salts such as sodium salt.

The irradiation may be performed in solution or in solid state. When irradiating a solution, the irradiation may be performed at preferably from about room temperature up to about reflux temperature. The organic solvent used for dissolution may be either polar protonic ($C_1$ to $C_4$ alcohol such as methanol or ethanol) or aprotonic (acetonitrile, tetrahydrofuran) in a mixture with water. Visible light irradiation of about 750 w at about 35° C. of aqueous acetonitrile solution of rosuvastatin calcium for about 7 hours gives a mixture of compounds (II and III) in the ratio 1:1. When irradiating in the solid state, the temperature is preferably from about 20EC to about 100EC. One of skill in the art may yet choose a narrow spectrum within these spectrums or a mixture of various spectrums. Based on the structural guidance provided herein of the various degradation products, one of skill in the art may prepare a synthetic route to obtain the degradation products.

In another embodiment, the corresponding lactone is obtained, either by irradiating the lactone form of rosuvastatin or by preparing the lactone from Compounds II and III to obtain the corresponding Compounds IV and V which can be used as a reference standard. Compound IV has the following $^1$H NMR (300 MHz, $CDCl_3$) δ (ppm): 1.24, 1.34, 1.68, 2.47, 2.53, 2.64, 3.15, 3.35, 3.46, 3.56, 3.60, 4.28, 4.45, 6.99, 7.14, 8.31; $^{13}$C NMR (75 MHz, $CDCl_3$) δ (ppm): 20.87, 21.26, 23.29, 31.41, 33.26, 34.03, 38.23, 42.07, 43.00, 62.23, 74.53, 115.61, 116.08 (J=26 Hz), 116.25 (J=22 Hz), 129.08, 128.91 (J=9 Hz), 139.28 (J=8 Hz), 157.64, 157.86, 163.96 (J=253 Hz), 169.47, 174.48; FAB+m/z ($MH^+$): 464. Compound V has the following $^1$H NMR (300 MHz, $CDCl_3$) δ (ppm): 1.24, 1.29, 1.52, 1.70, 2.58, 3.02, 3.21, 3.27, 3.41, 3.55, 3.60, 4.26, 4.78, 7.05, 7.12, 8.34; FAB+m/z ($MH^+$): 464.

The preparation of the corresponding lactone compounds IV and V from compound II and III includes dissolving compound II and III in a suitable solvent and forming a lactone ring for example with aqueous hydrochloric acid. Other acids may be used to form a lactone. A suitable solvent for preparation of the lactone from Compound II or III is dichloromethane, chloroform, acetonitrile or tetrahydrofuran. Preferably, the suitable solvent is acetonitrile. To recover the product, the solvent may be removed by any conventional process, such as evaporation. Obtained compounds IV and V can be separated by methods such as column chromatography and crystallization.

The preparation of the corresponding lactone compounds IV and V from rosuvastatin lactone may also be performed by visible light irradiation in the same solvents. The irradiation characteristics are as described above. The lactone compounds IV and V may be hydrolyzed with an equivalent amount of an aqueous base such as sodium or calcium hydroxide to obtain the corresponding salts in the presence of a solvent. Preferably, the solvent is acetonitrile. In one embodiment, the lactones are hydrolyzed with an aqueous solution of sodium hydroxide in acetonitrile, followed by removal of acetonitrile and addition of a source of calcium such as calcium chloride.

The lactone forms IV and V can be hydrolyzed with a base to obtain salts and thereafter converted to acid forms VI and VII, respectively, which can be used as a reference standard. The conversion of the lactones to salts may be carried out by using a basic aqueous solution. In one embodiment, the lactone is dissolved in a mixture of acetonitrile and an aqueous NaOH solution. The acetonitrile is then removed and a source of calcium such as calcium chloride is added to precipitate the calcium salt.

The acid forms are obtained after purifying the salt products by column chromatography on silica gel (as described in example 1). It is believed that the acidity of the silica column is responsible for the conversion. Compound VI has the following $^1$H NMR (600 MHz, CDCl$_3$+CD$_3$OD 5:1) δ (ppm): 1.25, 1.33, 1.39, 1.58, 2.22, 2.80, 2.89, 3.36, 3.52, 3.58, 3.61, 3.95, 7.01, 7.09, 8.26; $^{13}$C NMR (150 MHz, CDCl$_3$+CD$_3$OD 5:1) δ (ppm): 21.14, 21.31, 23.32, 31.56, 33.47, 40.15, 42.16, 42.97, 44.62, 68.99, 71.45, 115.17 (J=21 Hz), 116.32 (J=22 Hz), 117.77, 128.87 (J=9 Hz), 129.20, 142.34 (J=8 Hz), 157.71, 158.57, 164.26 (J=251 Hz), 174.30; Cl+m/z (MH$^+$): 482. Compound VII has the following $^1$H NMR (600 MHz, CDCl$_3$+CD$_3$OD 5:1) δ (ppm): 1.24, 1.31, 1.43, 2.25, 2.95, 3.05, 3.19, 3.30, 3.56, 3.60, 3.85, 4.03, 7.02, 7.08, 7.31; $^{13}$C NMR (150 MHz, CDCl$_3$+CD$_3$OD 5:1) δ (ppm): 21.15, 21.23, 22.98, 31.22, 33.36, 38.83, 42.08, 43.45, 68.82, 73.86, 114.95 (J=21 Hz), 116.31 (J=21 Hz), 117.41, 128.56 (J=8 Hz), 128.91, 142.02 (J=8 Hz), 157.58, 158.45, 164.28 (J=252 Hz), 173.19, 178; Cl+m/z (MH$^+$): 482.

The various forms of the degradation product may be purified so that only one stereoisomer is present. The R stereoisomer at position 6 is preferably at least about 95% free of the S stereoisomer % area by HPLC. Conversely, the S stereoisomer at position 6 is preferably at least about 95% free of the R stereoisomer % area by HPLC. Purification may be performed by column chromatography, TLC, HPLC, or other known purification methods.

Instruments

For chromatography, aluminum oxide or, preferably, silica gel may be used for packing. As for the eluent, different organic solvents or mixtures thereof may be used. Ethyl acetate is preferred.

Compounds II and III, isolated as corresponding acids (VI and VII), lactones (IV and V) can be investigated with $^1$H NMR, $^{13}$C NMR, COSY NMR and mass spectroscopic analyses to determine their structures.

EXAMPLES

Example 1

Preparation of Rosuvastatin Degradation Products by Irradiation of Rosuvastatin (Ca Salt)

1. Rosuvastatin (Ca-salt) (4.0 g) was dissolved in a mixture acetonitrile-water (380 ml-140 ml) and irradiated with visible light (750 w, 35° C.) for 7 hours. Acetonitrile and water were evaporated under vacuum.

2. The obtained solid was dissolved in 40 ml of acetonitrile and 40 ml of 1 N hydrochloric acid was added. The mixture was stirred at room temperature overnight. After evaporation of acetonitrile and water, and drying under vacuum, the obtained products were separated by column chromatography on silica gel (eluent hexane-ethyl acetate 1:2), giving lactone IV (0.8 g) and lactone V (0.6 g). TLC on silica gel, eluent hexane-ethyl acetate (1:2) R$_f$ 0.30 for Compound IV, R$_f$ 0.25 for Compound V.

| | Compound IV | | |
|---|---|---|---|
| | $^1$H NMR (CDCl$_3$) | $^{13}$C NMR (CDCl$_3$) | |
| Number atom | Δ | Δ | J(Hz) |
| 1 | | 169.47 | |
| 2 | 2.53, 2.64 | 38.23 | |
| 3 | 4.28 | 62.23 | |
| 4 | 1.68 | 34.03 | |
| 5 | 4.45 | 74.53 | |
| 6 | 3.15 | 43.00 | |
| 7 | 2.47, 3.46 | 23.29 | |
| 2' | | 157.64 | |
| 4' | | 157.86 | |
| 5' | | 115.61 | |
| 6' | | 174.48 | |
| 7' | 3.35 | 31.41 | |
| 8' | 1.24, 1.34 | 21.36, 20.87 | |
| 9' | 3.60 | 33.26 | |
| 10' | 3.56 | 42.07 | |
| 1" | | 129.08 | |
| 2" | | 139.28 | 8 |
| 3" | 6.99 | 116.25 | 22 |
| 4" | | 163.96 | 253 |
| 5" | 7.14 | 116.08 | 26 |
| 6" | 8.31 | 128.91 | 9 |

| | Compound V |
|---|---|
| | $^1$H NMR (CDCl$_3$) |
| Number atom | Δ |
| 2 | 2.58 |
| 3 | 4.26 |
| 4 | 1.52, 1.70 |
| 5 | 4.78 |
| 6 | 3.41 |
| 7 | 3.02, 3.21 |
| 7' | 3.27 |
| 8' | 1.24, 1.29 |
| 9' | 3.60 |
| 10' | 3.55 |

-continued

| | Compound V |
|---|---|
| | ¹H NMR (CDCl₃) |
| Number atom | Δ |
| 3" | 7.05 |
| 4" | |
| 5" | 7.12 |
| 6" | 8.34 |

3. Lactone IV (0.8 g) was dissolved in acetonitrile, and 1 N aqueous sodium hydroxide (4 ml) was added. The mixture was stirred at room temperature overnight. After evaporation of acetonitrile and water, and drying under vacuum, the obtained product was purified by column chromatography on silica gel (eluent dichloromethane-methanol 6.5 ml:10 ml), giving pure Compound VI (0.4 g).

| | Compound VI (Corresponding acid of Compound IV) | | |
|---|---|---|---|
| | ¹H NMR (CDCl₃ + CD₃OD 5:1) | ¹³C NMR (CDCl₃ + CD₃OD 5:1) | |
| Number atom | Δ | Δ | J (Hz) |
| 1 | | | |
| 2 | 2.22 | 42.97 | |
| 3 | 3.95 | 68.99 | |
| 4 | 1.39/1.58 | 40.15 | |
| 5 | 3.58 | 71.45 | |
| 6 | 2.89 | 44.62 | |
| 7 | 2.80/3.52 | 23.32 | |
| 2' | | 157.71 | |
| 4' | | 158.57 | |
| 5' | | 117.77 | |
| 6' | | 174.30 | |
| 7' | 3.36 | 31.56 | |
| 8' | 1.25/1.33 | 21.14/21.31 | |
| 9' | 3.61 | 33.47 | |
| 10' | 3.58 | 42.16 | |
| 1" | | 129.20 | |
| 2" | | 142.34 | 8 |
| 3" | 7.01 | 116.32 | 22 |
| 4" | | 164.26 | 251 |
| 5" | 7.09 | 115.17 | 21 |
| 6" | 8.26 | 128.87 | 9 |

4. Analogously, Compound VII (0.3 g) was obtained from lactone V.

| | Compound VII (Corresponding acid of Compound V) | | |
|---|---|---|---|
| | ¹H NMR (CDCl₃ + CD₃OD 5:1) | ¹³C NMR (CDCl₃ + CD₃OD 5:1) | |
| Number atom | Δ | Δ | J (Hz) |
| 1 | | 178 | |
| 2 | 2.25 | 42.08 | |
| 3 | 4.03 | 68.82 | |
| 4 | 1.43 | 38.83 | |
| 5 | 3.85 | 73.86 | |
| 6 | 3.05 | 43.45 | |
| 7 | 2.95/3.19 | 22.98 | |
| 2' | | 157.58 | |
| 4' | | 158.45 | |
| 5' | | 117.41 | |

-continued

| | Compound VII (Corresponding acid of Compound V) | | |
|---|---|---|---|
| | ¹H NMR (CDCl₃ + CD₃OD 5:1) | ¹³C NMR (CDCl₃ + CD₃OD 5:1) | |
| Number atom | Δ | Δ | J (Hz) |
| 6' | | 173.19 | |
| 7' | 3.30 | 31.22 | |
| 8' | 1.24/1.31 | 21.15/21.23 | |
| 9' | 3.60 | 33.36 | |
| 10' | 3.56 | 42.08 | |
| 1" | | 128.91 | |
| 2" | | 142.02 | 8 |
| 3" | 7.02 | 116.31 | 21 |
| 4" | | 164.28 | 252 |
| 5" | 7.08 | 114.95 | 21 |
| 6" | 8.31 | 128.56 | 8 |

Example 2

Preparation of Rosuvastatin Degradation Products by Irradiation of Rosuvastatin Lactone 1. rosuvastatin lactone 2.0 g) was dissolved in 200 ml of acetonitrile and irradiated with visible light (750 w, 35° C.) for 7 hours. After evaporation of the acetonitrile, and drying under vacuum, the obtained products were separated by column chromatography on silica gel (eluent hexane-ethyl acetate 1:2), giving lactone IV (1.1 g) and lactone V (0.6 g).

2. Lactone IV (1.0 g) was dissolved in 5 ml of acetonitrile and 2 ml of 1 N aqueous NaOH was added. The mixture was stirred at room temperature for 4 hours. After evaporation of acetonitrile, 1 ml of 2 N aqueous CaCl₂ was added, and the mixture was stirred for 1 hour at room temperature. The precipitate was filtered and dried under vacuum giving Compound II.

3. Analogously, Compound III was obtained from lactone V.

Example 3

HPLC Impurity Profile Determination of Rosuvastatin Calcium

The purity of Compounds IV, V, VI and VII is determined by HPLC analysis.

HPLC

Column: C18

Eluent: Gradient of Formate buffer and Acetonitrile

Flow: 1 ml/min

Detector: 245 nm

Sample volume: 10 ul

Diluent: Acetonitrile: Water=50:50

Mobile phase composition and flow rate may be varied in order to achieve the required system suitability.

Sample Preparation

About 10 mg of rosuvastatin calcium sample is weighed in a 20 ml amber volumetric flask. The sample is dissolved with 10 ml acetonitrile and diluted to volume with water.

Standard Preparation

About 10 mg of each Compounds IV, V, VI and VII are weighed in a 20 ml amber volumetric flask, dissolved with 10 ml acetonitrile and diluted to volume with water. 1 ml of prepared solution is diluted to 100 ml with diluent.

Method

The freshly prepared sample solutions are injected into the chromatograph, and the chromatogram of the sample is continued up to the end of the gradient. The areas for each peak in each solution is determined using a suitable integrator.

Having thus described the invention with reference to particular preferred embodiments and illustrated it with Examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. All references mentioned herein are incorporated in their entirety.

What is claimed is:

1. A lactone form of a rosuvastatin degradation product having the following structure:

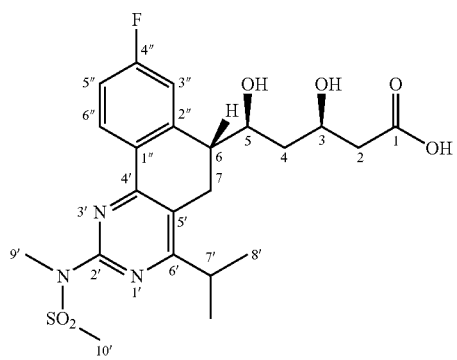

wherein, in the lactone form, $C^1$ and $C^5$ form an ester derivative of formula:

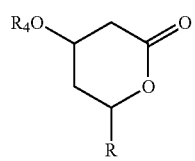

wherein $R_4$ is a hydrogen and R represents the rest of the structure of the rosuvastatin degradation product.

2. A mixture comprising (i) a lactone form of rosuvastatin degradation product I

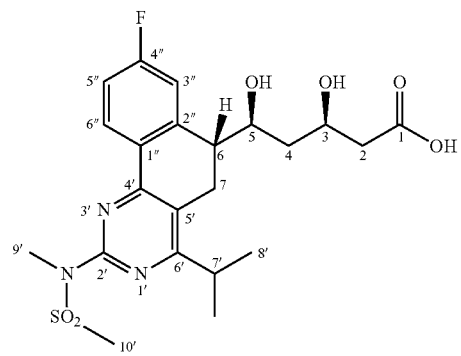

wherein, in the lactone form, $C^1$ and $C^5$ form an ester derivative of formula:

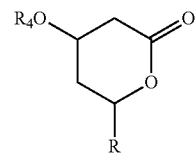

wherein $R_4$ is a hydrogen and R represents the rest of the structure of the rosuvastatin degradation product; (ii) a lactone form of rosuvastatin degradation product II

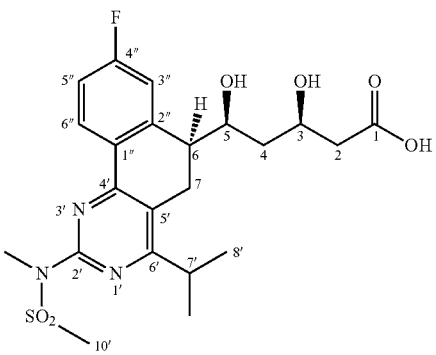

wherein, in the lactone form, $C^1$ and $C^5$ form an ester derivative of formula:

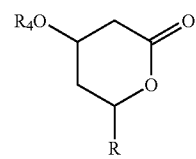

wherein $R_4$ is a hydrogen and R represents the rest of the structure of the rosuvastatin degradation product; and wherein the lactone form of rosuvastatin product II is less than 5% by HPLC in relation to product I in the mixture.

* * * * *